US010245280B2

(12) United States Patent
Macchi

(10) Patent No.: US 10,245,280 B2
(45) Date of Patent: Apr. 2, 2019

(54) USE OF HYALURONIC ACID FOR PREPARING COMPOSITIONS FOR TREATING ORAL CAVITY APHTHAS

(75) Inventor: Franco Macchi, Tradate (IT)

(73) Assignee: Bioplax Limited, London (GB)

( * ) Notice: Subject to any disclaimer, the term of this patent is extended or adjusted under 35 U.S.C. 154(b) by 0 days.

(21) Appl. No.: 10/561,670

(22) PCT Filed: Jun. 23, 2004

(86) PCT No.: PCT/EP2004/051209
§ 371 (c)(1),
(2), (4) Date: Dec. 19, 2005

(87) PCT Pub. No.: WO2005/000321
PCT Pub. Date: Jan. 6, 2005

(65) Prior Publication Data
US 2006/0147393 A1 Jul. 6, 2006

(30) Foreign Application Priority Data
Jun. 25, 2003 (IT) .......................... MI2003A001291

(51) Int. Cl.
*A61K 8/73* (2006.01)
*A61Q 11/00* (2006.01)
*A61K 31/715* (2006.01)

(52) U.S. Cl.
CPC ............ *A61K 31/715* (2013.01); *A61K 8/735* (2013.01); *A61Q 11/00* (2013.01)

(58) Field of Classification Search
None
See application file for complete search history.

(56) References Cited

U.S. PATENT DOCUMENTS

| 183,278 | A | 10/1876 | Banner | 514/54 |
| 5,972,906 | A | 10/1999 | Asculai et al. | 514/54 |
| 2002/0183278 | A1 | 12/2002 | Mastrodonato et al. | |

FOREIGN PATENT DOCUMENTS

| EP | 0444492 A1 | 4/1991 |
| EP | 0444492 | 9/1991 |
| EP | 0444492 B1 | 1/1996 |
| WO | WO0209637 | 2/2002 |

OTHER PUBLICATIONS

Stedman's Medical Dictionary 27th Edition, definition of aphtha.*
Merck Manual Home Edition. Mouth Sores.*
Saxen et al. Oral Surg Oral Med Oral Pathol Oral Radiol Endod 1997; 84:356-61.*
Vangelisti, Hyaluronic Acid in the Topical Treatment of Gingival Inflammations: Preliminary Clinical Trial, Translation of Attualità Terapeutica Internazionale No. 3—XY year—Apr. 1997.*
Barrons, Am J Health Syst Pharm. 2001;58(1).*
Screenshot of Mouth Ulcers home page with 'Message Board' highlighted, http://www.mouthulcers.org/message-board, downloaded from the internet Jun. 30, 2016.*
Screenshot of Mouth Ulcers home page, About the Mouth Ulcers Home Page, http://www.mouthulcers.org/about-mouth-ulcers-home-page, downloaded from the internet Jun. 30, 2016.*
Internet Archive Frequently Asked Questions, https://archive.org/about/faqs.php#The_Wayback_Machine, downloaded from the Internet Jun. 30, 2016.*
Leetaru, How Much of the Internet Does the Wayback Machine Really Archive? https://www.forbes.com/sites/kalevleetaru/2015/11/16/how-much-of-the-internet-does-the-wayback-machine-really-archive/#6fdf6aa94469, Nov. 16, 2015.*
Interview with Richard Thomas on Mouth Ulcers, http://www.mouthulcers.org/richardthomas.html, published Feb. 11, 2004.*
The Free Product Trial, Mouth Ulcers Message Board, http://www.mouthulcers.org/messages.php?thread=301&page=1 contains a message dated Jul. 10, 2003.*
Russell, A.L.; Parallelism between cutaneous and mucosal pathology. A new test bed for AT 2101 (3% diclofenac acid in 2.5% hyaluronan); Dec. 1, 1995.
Moseley, Waddington, "Periodontology: Hyaluronan and its Potential Role in Periodontal Healing"; Apr. 2002, vol. 29, No. 3.
Olivier; Suzannah; "Have a nice mouth"; The Times, Tuesday, Aug. 28, 2001.
Information for users of GENGIGEL provided by Oraldent (2003).
"Mouth ulcers"; excerpt from an internet forum; Jun. 21, 2003.
Nolan, A.; The efficacy of topical hyaluronic acid in the management of recurrent aphthous ulceration; J Oral Pathol Med (2006); 33: 461-5.
Stoopler, E.; "Recurrent Aphthous Stomatitis"; NYSDJ; Feb. 2003.
Internet Excerpt of 2.4 Dichlorbenzylalkohol, Nov. 10, 2009; http://www.pharmawiki.ch/wiki.
Wikipedia; definition of 2,4-Dichlorobenzyl alcohol; Oct. 10, 2009.
Wikipedia; Italian definition of "Afta"; 2011.
Wikipedia; English definition of "Afta"; 2011.
Wikipedia; German translation of "Aphthe"; Nov. 10, 2009.
Wikipedia; English definition of Aphthous ulcer; Jun. 29, 2007.
Wikipedia; Italian translation of definition of "Distribuzione della massa molare"; pp. 63-68; 2011.
Wikipedia; German translation of "Molmassenverteilung"; Nov. 3, 2008; pp. 1-5.
Wikipedia; English translation of "Molecular Weight Distribution"; 2011.
The Merck Manual, Centennial Edition, 1999.
Barrons RW; Treatment strategies for recurrent oral aphthous ulcer; AM J Health Syst Pharm, Jan. 1, 2001; 58(1): 41-50; quiz 51-3.
MEDgle web search; "What is aphtha"; Jun. 29, 2007.
Definition of "Stomatitis"; The free Dictionnary (on-line medical dictionary); Jun. 29, 2007.
Definition of Aphthous; Treatment Strategies for Recurrent Oral Aphthous Ulcer; www.medscape.com; Jun. 29, 2007.
"Aphthous Ulcer—Symptoms and Treatment"; excerpt from internet, pp. 1-3; Jun. 29, 2007.
Informative pamphlet of DermNet NZ retrieved from internet; New Zealand Dermatological Society Incorporated; 2003.
Mouth ulcers, Home Page—An interview with Richard Thomas; 2006.

(Continued)

*Primary Examiner* — Layla D Berry
(74) *Attorney, Agent, or Firm* — LeClairRyan PLLC

(57) ABSTRACT

Use of hyaluronic acid as the sole active ingredient for preparing compositions in particular for topical use for treating oral cavity aphthas.

7 Claims, No Drawings

(56) References Cited

OTHER PUBLICATIONS

Stephens, Anastasia; "Get your smile back"; Daily Mail; Aug. 21, 2001.
Region of Lombardy; Directorate—General of Health; Classification of diseases, of injuries, of surgical operations and of diagnostic and therapeutical procedures; Dec. 2002; pp. 1-3.
English translation Region of Lombardy; Directorate—General of Health; Classification of diseases, of injuries, of surgical operations and of diagnostic and therapeutical procedures; Dec. 2002; pp. 1-3.
Editorial of "Aphthous ulceration"; Journal of the Royal Society of Medicine; vol. 77; 1984.
Zain R.B.; Classification, epidemiology and aetiology of oral recurrent aphthous ulceration/stomatitis; Annal Dent Univ; Malaya 1999: 6: 34-37.
"L'acido ialuronico è la nouva arma contro le afte"; www.sanihelp.it/news/scheda/5830.html; Sep. 11, 2009.
English translation of "L'acido ialuronico è la nouva arma contro le afte"; www.sanihelp.it/news/scheda/5830.html; Sep. 11, 2009.
"Un nuovo approccio alla Sar"; www.sanihelp.it/news/scheda/5885.html; Sep. 11, 2009.
English translation of "Un nuovo approccio alla Sar"; www.sanihelp.it/news/scheda/5885.html; Sep. 11, 2009.
Norfolk and Norwich University Hospital; Department of Health; Norfolk and Norwich Hospital; Apr. 2004.
www.ortognatodonzia-it.com/afta.htr; "Afta, cause, cura e consigli"; Nov. 17, 2009.
English translation of www.ortognatodonzia-it.com/afta.htr; "Afta, cause, cura e consigli"; Nov. 17, 2009.
Pierfederici, Alessandra; Aftosi orale; www.springerlink.com; Apr. 29, 2007.
English translation of Pierfederici, Alessandra; Aftosi orale; www.springerlink.com, Apr. 29, 2007.
Russell A., "Parallelism Between Cutaneous and Mucosal Pathology. A New Test Bed for AT 2101 (3% Diclofenac Acid in 2.5% Hyaluronate)", *Royal Society of Chemistry, Round Table Series, Royal Society of Medicine Services*, London vol. 40, pp. 125-131 (1995).

\* cited by examiner

USE OF HYALURONIC ACID FOR PREPARING COMPOSITIONS FOR TREATING ORAL CAVITY APHTHAS

This application is a national stage application under 35 U.S.C. § 371 of PCT Application No. PCT/EP2004/051209, filed Jun. 23, 2004, which claims priority of Italy Application No. MI2003A001291, filed Jun. 25, 2003, which are hereby incorporated by reference in their entirety.

FIELD OF THE INVENTION

The present invention relates to the use of hyaluronic acid for treating oral cavity aphthas.

STATE OF THE ART

Aphthas, better known as recurrent oral aphthous ulcerations (ROAU), are ulcerous pathologies of the oral mucosa which affect more than 20% of the population. The etiology of this ailment is yet to be defined. Aphthas are round or oval protuberant ulcers, surrounded by bright red areolas, on the smooth tissue of the mucosa. Almost all types of aphthas, including small ones, are capable of causing pain.

Of the susceptible individuals one in ten will have monthly episodes, whereas the majority have 3-4 episodes of new lesions per year occur. Untreated lesions in general last for 7-10 days and heal without leaving scars. In general, aphtha treatments are intended to ease symptoms, although many types of therapies for treating aphthas have been considered.

For example analgesics for topical use have been employed for relieving symptoms, and anti-inflammatories for reducing pathological changes, while anti-bacterials have been contemplated for controlling microbial contaminations and secondary infections.

Anti-bacterial agents include antibiotics (tetracycline) and antiseptics (clorhexidine).

Mouthwashes containing wide spectrum antibiotics have been able to reduce new ulcers, following a 10 day treatment. This effect is due to a reduced oral microflora thereby reducing the effects of a secondary infection.

However, antibiotics have a potentially undesirable mycotic effect and can give rise to allergic reactions.

Anti-bacterial mouthwashes can provide some benefit by controlling pain, reducing both the effects caused by a secondary infection and the duration of the ulcer. Clorhexidine can reduce the total number of days with ulceration, but has not been at all effective on the incidence or severity thereof. Furthermore, it frequently gives rise to colour changes on the teeth and tongue and upsets taste sensation.

Hyaluronic acid is a natural constituent of connective tissue.

EP-A1-0444492 describes the topical use of high molecular weight hyaluronic acid for treating inflammatory diseases of the oral cavity, such as gingivitis.

WO 0209637 discloses pharmaceutical compositions for the topical treatment of inflammatory diseases of the oral mucosa such as stomatitis, containing an association of hyaluronic acid, glycyrrhetinic acid and polyvinylpyrrolidone

SUMMARY OF THE INVENTION

The Applicant has found that hyaluronic acid is able to effectively cure oral cavity aphthas.

In this respect, the Applicant has surprisingly found that hyaluronic acid is not only able to alleviate the symptoms and reduce the duration of ulceration, as well as the severity thereof.

An aspect of the present invention is therefore the use of hyaluronic acid for preparing compositions, in particular for topical use, for treating oral cavity aphthas.

DETAILED DESCRIPTION OF THE INVENTION

The compositions containing hyaluronic acid for use in accordance with the invention are preferably liquid, solid and/or semisolid preparations in the form of O/W (oil in water) and W/O (water in oil) emulsions, ointments and creams, pastes, gels, solutions, suspensions, dispersions, powders, tensiolytes, oleolytes, or any other Theological form suitable for use alone or in combination with the other forms, also in the form of tablets, pills, gums, or in the form of any other applicative solutions known in the art and suitable for topical use in the oral cavity.

Even more preferably, the topical compositions for use in accordance with the present invention are in the form of oral cavity gels, mouthwashes and sprays. Preferably hyaluronic acid is in the form of the sodium salt. Hyaluronic acid has preferably a molecular weight of between 800,000 and 4,000,000, even more preferably between 1,000,000 and 2,000,000.

The topical compositions of the present invention preferably contain hyaluronic acid in the form of the sodium salt at concentrations of between 0.01 and 10% by weight on the total weight of the composition, more preferably between 0.01 and 5% by weight.

Some illustrative but non-limiting examples of compositions for topical use based on sodium hyaluronate are given.

| Composition 1: gel | |
|---|---|
| Sodium hyaluronate average molecular weight 1,500,000: | 0.240 w/w |
| Xylitol | 7.500 w/w |
| Sodium carboxymethylcellulose | 4.500 w/w |
| PEG 40 hydrogenated castor oil | 1.000 w/w |
| Glyceryl monolaurate | 0.700 w/w |
| Polycarbophil | 0.800 w/w |
| Lactic acid (Pharm.) | 0.060 w/w |
| Sodium lactate | 0.100 w/w |
| EDTA | 0.050 w/w |
| Sodium saccharinate | 0.220 w/w |
| Flavour | 0.500 w/w |
| Dichlorobenzylalcohol | 0.500 w/w |
| Colorant CI 42090 (FD&C BLUE 1) | 0.00012 w/w |
| Colorant CI 47005 (D&C YELLOW 10) | 0.00028 w/w |
| Sodium hydroxide | to pH = 6.5 |
| Water | remainder to 100 |
| Composition 2: mouthwash | |
| Sodium hyaluronate average molecular weight 1,500,000: | 0.025 w/w |
| Xylitol | 7.500 w/w |
| PEG 40 hydrogenated castor oil | 0.600 w/w |
| Polycarbophil | 0.150 w/w |
| Lactic acid (Pharm.) | 0.060 w/w |
| Sodium lactate | 0.100 w/w |
| EDTA | 0.050 w/w |
| Sodium saccharinate | 0.018 w/w |
| Flavour | 0.100 w/w |
| Dichlorobenzylalcohol | 0.500 w/w |
| Polysorbate 20 | 0.800 w/w |
| Colorant CI 42090 (FD&C BLUE 1) | 0.00012 w/w |
| Colorant CI 47005 (D&C YELLOW 10) | 0.00028 w/w |

| | |
|---|---|
| Sodium hydroxide | to pH = 6.5 |
| Demineralized Water | remainder to 100 |
| Composition 3: spray | |
| Sodium hyaluronate | 0.100 w/w |
| Xylitol | 7.500 w/w |
| PEG 40 hydrogenated castor oil | 0.500 w/w |
| Dichlorobenzylalcohol | 0.500 w/w |
| Lactic acid (Pharm.) | 0.060 w/w |
| Sodium lactate | 0.100 w/w |
| EDTA | 0.050 w/w |
| Sodium saccharinate | 0.220 w/w |
| Flavour | 0.200 w/w |
| PVA | 0.050 w/w |
| Propylene glycol | 4.000 w/w |
| Sodium hydroxide | to pH = 6.5 |
| Demineralized water | remainder to 100 |

Clinical Study
A) Study Design

This controlled study used a double blind, single centre, parallel group design to determine the efficacy of a gel formulation in relieving the symptoms in subjects with recurrent oral aphthous ulceration.

B) Study Population
B1) Number of Subjects

The investigator enrolled a sufficient number of subjects in the study to achieve a study population of 120 evaluable subjects (60 in each group) with ROAU.

B2) Subject-Selection Criteria

Inclusion Criteria To be eligible for study partecipation the subject had to meet the following criteria:
The subject must be between 18 and 65 years of age
A history of ROAU >2 times per year
Current aphthous ulcer/ulcers present for <3 day B3) Exclusion Criteria Any of the following conditions excluded subjects from eligibility for study partecipation:
Patients with underlying white blood cell disorder
Patients taking systemic hemotherapy, immunosuppressants, or who sufer from drug-related recurrent aphthous ulceration
Patients suffering from malignant disease
Patients with uncorrected dietary defect
Pregnant or breast feeding women
A history of sensitivity of mouthwashes B4) Prohibited/Allowable Medications
Prohibited Medications
Any topical or systemic treatment for ROAU including steroids and vitamins B1 and B6 other than study treatments
Antiseptic mouthwashes
Systemic chemotherapy, immunosuppressants
Rx or OTC nonsteroidal anti-inflammatory drugs including, but not limited to aspirin, diclofenac, diflunisal, etodolac, ibuprofen, indomethacin, ketoprofen, ketorolac, nabumetone, naproxen, naproxen sodium, oxaprozin, piroxicam, or sulindac.
Allowable Medications
Any medication not specifically prohybited
Paracetamol C) Study Methodology Subjects were recruited from an existing group of patients with ROAU who have been screened for known causative factors or when they present as new patients to the clinic. Existing patients or patients attending screening who do not have a current ulcer will be asked to contact the clinic at the time of onset of their next aphthous ulcer.

C1) Clinic Visit 1 (Day 1): Screened subjects meeting the selection criteria for the study described had the study explained to them and if they agreed to partecipate signed an informed consent form. They will be allocated a subsequential subject number. The subjects demographic history and history of ROAU were recorded together with details of their current episode of aphthous ulceration including the time and date of onset, number, size and position of mouth ulcers.

The study nurse explained to the subjects how to fill out the 10 cm visual analogue scale (VAS) used to score their level of discomfort or soreness arising from their mouth ulcer. Subjects recorded their discomfort from their ulcer prior to gel application (baseline). They applied the gel to the ulcerated area under supervision with 1-2 ml of their assigned gel having one of the following two composition:

| Product name | Ingredients |
|---|---|
| Hyaluronic Acid Gel 0.2% | Aqua, xylitol, cellulose gum, alcohol, PEG-40, Hydrogenated castor oil, sodium hyaluronate, Polyvinyl alcohol, polycarbophil, Dichlorobenzyl alcohol, aroma flavouring CI 40290 |
| Placebo | Aqua, xylitol, cellulose gum, alcohol, PEG-40, Hydrogenated castor oil, Polyvinyl alcohol, polycarbophil, Diclorobenzyl alcohol, aroma flavouring |

Subjects recorded their discomfort immediately after application and at 5, 10, 15, 20, 30, 45 and 60 minutes. The time of gel application will be recorded in the CRF and the subjects log diary. A stopwatch was used to record time measurements.

The subject will be supplied with sufficient tubes of the gel to take home. The study nurse instructed the subject how to fill out a log diary. The subject continued to record their VAS scores in their log diary at 2, 3 and 4 hours postgel application. The subjects will apply the gel again after their evening meal and record their VAS score 1 hour post application.

Appendix A; Time table of Visits and Procedures
C2) Day 2-7

Subjects continued to apply the gel at home 2 to 3 time daily, after breakfast and after their evening meal (and 1 other time during the day, if desired) from days 2-7, even if their ulcer has healed. VAS scores was recorded in the subjects' log diaries 1 hour post application in the morning and evening. Subjects recorded the severity of their mouth ulcers, any unpleasant effects of their study treatment and the severity of their mouth ulcers. Any new ulcers occurring was recorded in their log diaries.

C3) Clinic Visit 2 (Day 8):

Subjects returned to the clinic to review their completed log diaries with the study nurse and return remaining study material. They were asked to score their overall assessment of the gel on a 5 point scale. Subjects will be questioned about the occurrence of any adverse events.

Information obtained relating to adverse events were recorded on the associated pages of the CRF. The size, number and position of lesions present on day 8 were recorded on the CRF.

The VAS entries on each subjects log diary were measured and transcribed to the associated pages of the CRF.

C4) Efficacy Assessments

Following entry to the study, the study nurse recorded the subject's demographic details and examined the subject to determine the size, number and position of ulcers and record time of onset of ulcer.

C5) Primary Efficacy Parameter

Subjects recorded their discomfort/soreness scores on a 10 cm visual analogue scale (VAS).

The boundaries of the scales were "worst possible" and "no soreness".

Scores were completed at baseline and at 0, 5, 10, 15, 20, 30, 45 and 60 minutes post initial application. The gel application and completion of scores was done under supervised conditions in the Clinic. At the end of 60 minutes, the subjects continued to apply the gel at home 2 to 3 times daily and they were asked to record discomfort/soreness on the same VAS twice daily an hour after the morning and evening applications.

Two parameters were extrapolated from the serial VAS completed in the first hour:
a) Time in minutes to the maximum reduction in discomfort/soreness following dosing with the gel.
b) Serial VAS recorded in the first hour was compiled into a graph of discomfort soreness (mm) versus time (minutes). The area under the graph was measured using the trapezoidal method and recorded as AUC (0-60 minutes). This provided an overall assessment of each subjects discomfort/soreness experience throughout the initial observation period.

C6) Secondary Efficacy Parameter

At the end of the 7 day investigation period, subjects were asked if they have had any ulcer free days and their overall assessment of the gel based on the following scale:

Very good Good Moderate Poor Very Poor

D) Results

In this randomized blind clinical study it was evidenced that if compared to placebo composition the gel composition containing hyaluronic acid proved able to reduce significantly the number of ulcers already in the fifth day, and also evidenced an overall beneficial effect in every investigated ROAU symtphomatology.

The invention claimed is:

1. A method of reducing the number of ulcers in a subject having an episode of Recurrent Oral Aphthous Ulcers (ROAU) said method comprising the steps of:
   selecting a subject having an episode of ROAU; and
   administering, repeatedly to the selected subject, from the first day to the seventh day of the episode of ROAU, a composition comprising between 0.01 and 1% by weight hyaluronic acid or a salt thereof, said hyaluronic acid or salt thereof being the sole active ingredient and having an average molecular weight of between 800,000 and 4,000,000,
   wherein said composition is administered in an amount sufficient to reduce the number of ulcers in the subject by the fifth day of said single episode.

2. The method as claimed in claim 1, wherein the hyaluronic acid is administered in the form of sodium salt.

3. The method as claimed in claim 2 wherein said hyaluronic acid sodium salt is topically administered.

4. The method according to claim 3 wherein said hyaluronic acid is administered in the form of topical compositions containing sodium hyaluronate in concentrations between 0.01 and 1% by weight on the total weight of the compositions.

5. The method according to claim 1, wherein said average molecular weight of hyaluronic acid is between 1,000,000 and 2,000,000.

6. The method according to claim 1, wherein said administering reduces the occurrence of new aphthous ulcers.

7. The method of claim 1, wherein said administering is carried out at least twice daily.

* * * * *